(12) United States Patent
Kanaya et al.

(10) Patent No.: US 10,130,579 B2
(45) Date of Patent: Nov. 20, 2018

(54) COSMETIC MATERIAL

(71) Applicant: Dow Corning Toray Co., Ltd., Tokyo (JP)

(72) Inventors: Yuichi Kanaya, Tokyo (JP); Jun Miyano, Tokyo (JP); Akihiro Nakano, Tokyo (JP); Yusuke Narita, Tokyo (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 0 days.

(21) Appl. No.: 15/303,743

(22) PCT Filed: Apr. 8, 2015

(86) PCT No.: PCT/JP2015/060963
§ 371 (c)(1),
(2) Date: Oct. 13, 2016

(87) PCT Pub. No.: WO2015/159773
PCT Pub. Date: Oct. 22, 2015

(65) Prior Publication Data
US 2017/0035681 A1    Feb. 9, 2017

(30) Foreign Application Priority Data
Apr. 15, 2014 (JP) ................. 2014-084003

(51) Int. Cl.
| A61K 8/891 | (2006.01) |
| A61K 8/49 | (2006.01) |
| A61K 8/29 | (2006.01) |
| A61K 8/34 | (2006.01) |
| A61K 8/19 | (2006.01) |
| A61Q 1/00 | (2006.01) |
| A61K 8/36 | (2006.01) |
| A61K 8/02 | (2006.01) |
| A61Q 17/04 | (2006.01) |

(52) U.S. Cl.
CPC ............ *A61K 8/891* (2013.01); *A61K 8/0241* (2013.01); *A61K 8/19* (2013.01); *A61K 8/29* (2013.01); *A61K 8/342* (2013.01); *A61K 8/361* (2013.01); *A61K 8/498* (2013.01); *A61Q 1/00* (2013.01); *A61Q 17/04* (2013.01)

(58) Field of Classification Search
None
See application file for complete search history.

(56) References Cited

U.S. PATENT DOCUMENTS

| 4,980,167 A | 12/1990 | Harashima et al. |
| 5,596,061 A | 1/1997 | Berger et al. |
| 5,628,989 A | 5/1997 | Harashima et al. |
| 5,939,478 A | 8/1999 | Beck et al. |
| 6,238,656 B1 | 5/2001 | Morita et al. |
| 2003/0212232 A1 | 11/2003 | Majeti et al. |
| 2009/0253885 A1 | 10/2009 | Kamei |
| 2010/0190871 A1 | 7/2010 | Araki et al. |
| 2011/0182846 A1* | 7/2011 | Ikeda ............... A61K 8/11 424/78.03 |
| 2012/0040931 A1 | 2/2012 | Kamei et al. |
| 2014/0255323 A1* | 9/2014 | Ishida ............... A61K 8/27 424/59 |
| 2014/0348765 A1* | 11/2014 | Sasaki ............... A61K 8/27 424/59 |
| 2015/0157546 A1 | 6/2015 | Naoi |

FOREIGN PATENT DOCUMENTS

| JP | H02243612 A | 9/1990 |
| JP | H0812524 A | 1/1996 |
| JP | H0812545 A | 1/1996 |
| JP | H0812546 A | 1/1996 |
| JP | H08109263 A | 4/1996 |
| JP | H09241511 A | 9/1997 |
| JP | H11504665 A | 4/1999 |
| JP | H11193331 A | 7/1999 |
| JP | 2000281523 A | 10/2000 |
| JP | 200189347 A | 4/2001 |
| JP | 2002114849 A | 4/2002 |
| JP | 2004026669 A | 1/2004 |
| JP | 2004091423 A | 3/2004 |
| JP | 2005524747 A | 8/2005 |
| JP | 2007277415 A | 10/2007 |
| JP | 2009263643 A | 11/2009 |
| JP | 2010138074 A | 6/2010 |
| JP | 2012036348 A | 2/2012 |
| JP | 2013121947 A | 6/2013 |
| JP | 2013177370 A | 9/2013 |

(Continued)

OTHER PUBLICATIONS

PCT/JP2015/060963 International Search Report dated Jul. 14, 2015, 2 pages.
English language abstract and machine translation for JPH0812524(A) extracted from http://worldwide.espacenet.com database on Oct. 25, 2016, 13 pages.
English language abstract and machine translation for JPH0812546 (A) extracted from http://worldwide.espacenet.com database on Oct. 25, 2016, 12 pages.
English language abstract and machine translation for JPH08109263 (A) extracted from http://worldwide.espacenet.com database on Oct. 25, 2016, 24 pages.

(Continued)

*Primary Examiner* — Ernst V Arnold
*Assistant Examiner* — Kyung S Chang
(74) *Attorney, Agent, or Firm* — Warner Norcross & Judd LLP

(57) ABSTRACT

A cosmetic material comprises (A) a hydrophobic powder; (B) a carboxylic acid modified silicone; (C) a basic compound; and (D) water. The (A) hydrophobic powder is generally dispersed in an aqueous phase of the cosmetic material. The cosmetic material can provide a refreshing sense of feel during use, and can form a cosmetic film with excellent water resistance on the skin.

19 Claims, No Drawings

(56) References Cited

FOREIGN PATENT DOCUMENTS

| WO | WO2009022621 A1 | | 2/2009 | | |
| WO | WO2009025146 A1 | | 2/2009 | | |
| WO | WO-2012070309 A1 | * | 5/2012 | ............ | A61K 8/062 |
| WO | WO-2013061776 A1 | * | 5/2013 | ............ | A61K 8/27 |
| WO | WO2013100177 A1 | | 7/2013 | | |
| WO | WO-2013108515 A1 | * | 7/2013 | ............ | A61K 8/27 |

OTHER PUBLICATIONS

English language abstract and machine translation for JPH09241511 (A) extracted from http://worldwide.espacenet.com database on Oct. 25, 2016, 13 pages.

English language abstract and machine translation for JP2002114849 (A) extracted from http://worldwide.espacenet.com database on Oct. 25, 2016, 10 pages.

English language abstract and machine translation for JP2004026669 (A) extracted from http://worldwide.espacenet.com database on Oct. 25, 2016, 12 pages.

English language abstract and machine translation for JP2004091423 (A) extracted from http://worldwide.espacenet.com database on Oct. 25, 2016, 6 pages.

K. Kageshima et al., Fragrance Journal, Special Issue Nov. 19, 2005, p. 125-130.

English language abstract for JP2010138074 (A) extracted from http://worldwide.espacenet.com database on Oct. 25, 2016 and machine translation extracted from https://patents.google.com database on Jan. 13, 2017, 20 pages.

English language abstract and machine translation for JP2007277415 (A) extracted from http://worldwide.espacenet.com database on Jun. 4, 2018, 29 pages.

English language abstract and machine translation for JP2013177370 (A) extracted from http://www.j-platpat.inpit.go.jp database on Jun. 5, 2018, 20 pages.

\* cited by examiner

COSMETIC MATERIAL

CROSS-REFERENCE TO RELATED APPLICATIONS

This application is the National Stage of International Application No. PCT/JP2015/060963 filed on 8 Apr. 2015, which claims priority to and all advantages of Japanese Patent Application No. 2014-084003 filed on 15 Apr. 2014, the content of which is hereby incorporated by reference.

FIELD OF THE INVENTION

The present invention relates to a cosmetic material containing an aqueous phase, where a hydrophobic powder is dispersed in the aqueous phase.

BACKGROUND OF THE INVENTION

A cosmetic material containing an aqueous phase as a continuous phase will provide a moist refreshing feel during use, and therefore is widely used in basic cosmetics such as emulsions, base layer cosmetics, foundation cosmetics, and makeup cosmetics such as eyeshadow or the like.

On the other hand, these cosmetic materials normally use a hydrophilic surfactant, hydrophilic powder, and the like, and there is a problem that the cosmetic film obtained by applying this cosmetic material has poor water resistance.

Therefore, addition of a hydrophobic powder that has been hydrophobic treated is proposed in Japanese Unexamined Patent Application 2004-91423, for example, in order to provide water resistance to the cosmetic film in a cosmetic material containing an aqueous phase.

However, the surface of the hydrophobic powder is non-hydrophilic, so dispersing the hydrophobic powder in the aqueous phase is difficult, and there is a problem that the hydrophobic powder will fluctuate and precipitate over time and will phase separate.

Incidentally, PCT International Publication No. WO 2009/022621 discloses surface treatment of a powder using carboxylic acid modified silicone, but the purpose is to provide water resistance by fixing a carboxylic acid modified silicone as a polyvalent metal salt on the powder surface, using the carboxylic acid modified silicone as a dispersing agent for the hydrophobic powder in the aqueous phase, and controlling the surfactant effect or dispersing effect by controlling the carboxylic acid variable site of the carboxylic acid modified silicone.

Furthermore, Kageshima Kazumi et al. (Kageshima Kazumi, Shimizu Toshiyuki, Fragrance Journal, Special Issue No. 19, 2005, p. 125-130) discloses that a carboxyl modified silicone neutralized by triethanolamine will have excellent emulsifying capacity, but there is no mention of a function as a dispersing agent for dispersing the hydrophobic powder in the aqueous phase.

SUMMARY OF THE INVENTION

Technical Problem

An object of the present invention is to provide a cosmetic material with a hydrophobic powder favorably dispersed in an aqueous phase, that provides a refreshing feel during use, and that can form a cosmetic film with excellent water resistance on the skin.

Technical Solution

The object of the present invention can be achieved by the cosmetic material comprising the following forms:

(A) hydrophobic powder;
(B) carboxylic acid modified silicone;
(C) a basic compound; and
(D) water;
wherein the (A) hydrophobic powder is dispersed in the aqueous phase.

The cosmetic material of the present invention preferably contains (A) hydrophobic powder within a range of 1 to 40 mass %.

Incidentally, in the present specification, "mass %" is the same meaning as "weight %", and the reference is the total mass (total weight) of the cosmetic material of the present invention, unless otherwise expressly noted.

The cosmetic material of the present invention preferably contains the (B) carboxylic acid modified silicone within a range of 0.01 to 20 mass parts with regard to 10 mass parts of the hydrophobic powder.

The (B) carboxylic acid modified silicone has the following structural formula (A):

[Formula 1]

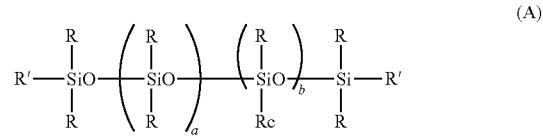

[where, Rc represent an organic group containing a carboxyl group expressed by the general formula $-R^1-(OR^2)_p-(O)_w-R^3-COOH$ ($R^1$ represents a straight chain or branched alkylene group with 2 to 22 carbon atoms; $R^2$ represents a straight chain or branched alkylene group with 2 to 4 carbon atoms; $R^3$ represents a bond (—) or a straight chain or branched alkylene group with 1 to 22 carbon atoms; p represents a number between 0 and 200; and w represents a number of 0 or 1;

R represents the same or different alkyl or alkoxy with 1 to 22 carbon atoms, or phenyl group, R' represents Rc or R, a and b represent a number within a range of 0 or higher, where a+b represents a number within a range of 0 to 1000, with the proviso that when b=0, at least one of R' is Rc.

The cosmetic material of the present invention preferably contains the (D) water within a range of 20 to 95 mass %.

The pH of the cosmetic material of the present invention is preferably 7.1 to 9.5.

The cosmetic material of the present invention may also contain (G) a polyhydric alcohol.

The cosmetic material of the present invention preferably also contains (E) an oily agent. In this case, the cosmetic of the present invention preferably contains the (E) oily agent within a range of 3 to 60 mass %.

The cosmetic material of the present invention preferably also contains (F) a higher fatty acid salt. In this case, the cosmetic material of the present invention preferably contains (F) a higher fatty acid salt within a range of 0.1 to 12 mass %. The higher fatty acid is preferably one selected from isostearic acid, hexyldecanoic acid, and oleic acid.

The cosmetic material of the present invention may also contain (H) a water-soluble thickening agent.

The cosmetic material of the present invention preferably does not contain a surfactant other than the (B) carboxylic acid modified silicone. Furthermore, if the cosmetic material of the present invention contains (F) a salt of a higher fatty acid, the cosmetic material preferably does not contain a surfactant other than the (B) carboxylic acid modified silicone and the (F) salt of a higher fatty acid.

The cosmetic material of the present invention preferably is in the form of an oil in water emulsion composition.

Furthermore, the present invention relates to a method of manufacturing a cosmetic material, containing a step of producing an aqueous dispersion where the (A) hydrophobic powder is dispersed in an aqueous phase, by first blending the (A) hydrophobic powder, (B) carboxylic acid modified silicone, (C) basic compound, and (D) water.

If the cosmetic material contains (G) a polyhydric alcohol, the method of manufacturing the cosmetic material of the present invention preferably includes a step of producing an aqueous dispersion where the (A) hydrophobic powder is dispersed in an aqueous phase, by first mixing the (A) hydrophobic powder, (B) carboxylic acid modified silicone, (C) basic compound, (D) water, and (G) polyhydric alcohol.

The pH of the aqueous dispersion is preferably within a range of 6.5 to 14.0.

Furthermore, if the cosmetic material contains (G) a polyhydric alcohol, the method of manufacturing the cosmetic material of the present invention may include a step of obtaining a mixture by first mixing the (G) polyhydric alcohol, (A) hydrophobic powder, and (B) carboxylic acid modified silicone, and a step of mixing the (C) basic compound and the (D) water into the mixture.

Furthermore, if the cosmetic material contains (G) a polyhydric alcohol, the method of manufacturing the cosmetic material of the present invention may include a step of producing an aqueous dispersion with the pH in a range of 6.5 to 14 where the hydrophobic powder is dispersed in an aqueous phase, by mixing the (C) basic compound and the (D) water into the mixture obtained by a step of first mixing the (G) polyhydric alcohol, (A) hydrophobic powder, and (B) carboxylic acid modified silicone.

Advantageous Effect of Invention

The cosmetic material of the present invention has an aqueous phase, and the hydrophobic powder is preferably dispersed in the aqueous phase. Therefore, the hydrophobic powder will not flocculation over time.

Furthermore, the cosmetic material of the present invention can provide a refreshing sense of feel during use, and can form a cosmetic film with excellent water resistance on the skin. Furthermore, a water-based cosmetic material that conventionally has been difficult to design using hydrophobic powder because of the relationship to dispersibility, can be provided with excellent hydrophobic powder dispersibility and appearance and can provide the excellent water repellency and water resistance of the hydrophobic powder onto the skin.

DESCRIPTION OF EMBODIMENTS

As a result of extensive research, the present inventors discovered that by combining a hydrophobic powder, carboxylic acid modified silicone, a basic compound, and water, the hydrophobic powder can be favorably dispersed in an aqueous phase by the action of carboxylic acid modified silicone as a surfactant or dispersing agent, and when this mixture is applied to the skin, the carboxylic acid modified site of the carboxylic acid modified silicone will convert from a carboxylic acid salt to a free carboxylic acid by the weak acidity of the skin itself, the surfactant capability or dispersing capability will drop, the hydrophobic powder can be deposited on the skin, and a hydrophobic film will be formed on the skin, and thus the present invention was achieved.

In particular, the cosmetic material with excellent dispersibility and long-term storage stability can be favorably obtained by uniformly blending a hydrophobic powder, carboxylic acid modified silicone, and polyhydric alcohol, then adding a basic compound and water and adjusting the pH to a range of 6.5 to 14.0.

If the cosmetic material of the present invention contains an oily agent, the oily agent will also be deposited on the skin with the hydrophobic powder when the cosmetic material of the present invention is applied to the skin, and will form a hydrophobic film, and the adhesion thereof can be enhanced. If the cosmetic material of the present invention contains an oily agent, a surfactant is preferably included as an emulsifying agent.

If the cosmetic material of the present invention contains a salt of a higher fatty acid, the dispersion of the hydrophobic powder in the aqueous phase can be more favorably achieved due to the surfactant effect of the salt before applying to the skin. Furthermore, if the cosmetic material of the present invention contains an oily agent, the salt of the higher fatty acid will function as a favorable emulsifying agent, but after applying to the skin, the salt will convert to a free higher fatty acid, the hydrophobic powder (and oily agent) will be deposited together on the skin, and the hydrophobic film with more excellent water resistance can be formed.

If the cosmetic material of the present invention contains a polyhydric alcohol and/or a water-soluble thickening agent, the dispersibility of the hydrophobic powder in the aqueous phase can be further enhanced.

If the cosmetic material of the present invention does not contain a surfactant other than the carboxylic acid modified silicone, or if the cosmetic material of the present invention contains the salt of an upper fatty acid, does not contain a surfactant other than the carboxylic acid modified silicone and the salt of a higher fatty acid, the water resistance of the cosmetic film obtained on the skin by the cosmetic material of the present invention can be further enhanced.

The surfactant other than the surfactant components that must be included in the cosmetic material of the present invention (component (B) or components (B) and (F)) is not particularly restricted, but an anionic, cationic, nonionic, or amphoteric surfactant can be suggested.

Incidentally, with the present invention, the phrase "does not contain" means essentially does not contain, and herein, "essentially" means that an amount of 5 mass % or less of the total mass of the cosmetic material of the present invention can be included. However, a smaller amount is advantageous, and the amount is preferably 3 mass % or less, more preferably 2 mass % or less, and even more preferably 1 mass % or less. It is most preferable that the cosmetic material of the present invention not contain any surfactant other than the surfactants that are required (component (B) or components (B) and (F)).

The cosmetic material of the present invention will be described below in further detail.

[Hydrophobic Powder]

The cosmetic material of the present invention contains at least one of (A) hydrophobic powder.

The "powder" in the present invention is generally used as a component in cosmetic materials, and includes white or colored pigments, fine particles such as ultraviolet light dispersing agents or the like (including so-called nanoparticles), and extender pigments. The white and colored pigments are used for coloring the cosmetic material or the like, but on the other hand, the extender pigments are used for modifying the feel or the like of the cosmetic material. The "powder" of the present invention can be white or colored pigment that is normally used in cosmetic materials, or can be and extender pigment, without restriction. One or more of powder is preferably added.

The shape of the powder (spherical, rodlike, needlelike, platelike, irregular shape, spindle shape, and the like), the particle diameter (fumed, fine particle, pigment grade, and the like), and the particle structure (porous, nonporous, and the like) are not restricted in any way, but the average primary particle size is preferably within a range of 1 nm to 100 nm.

The powder can be an inorganic powder, organic powder, surfactant metal salt powder (metal soap), colored pigment, pearl pigment, metal powder pigment, and the like, and a compound of these can also be used. Specific examples of the inorganic powder include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic anhydride, aluminum silicate, sodium silicate, sodium magnesium silicate, magnesium silicate, aluminum magnesium silicate, calcium silicate, barium silicate, strontium silicate, tungstenite metal salts, hydroxyapatite, vermiculite, Higilite, bentonite, montmorillonite, hectorite, zeolite, ceramic powder, dicalcium phosphate, alumina, aluminum hydroxide, boron nitride, boron nitride, and the like;

examples of organic powders include polyamide powder, polyester powder, polyethylene powder, polypropylene powder, polystyrene powder, polyurethane powder, benzoguanamine powder, polymethyl benzoguanamine powder, polytetrafluoroethylene powder, polymethyl methacrylate powder, cellulose, silk powder, nylon powder, 12 nylon, 6 nylon, silicone powder, polymethylsilsesquioxane spherical powder, styrene-acrylic acid copolymer, divinylbenzene-styrene copolymer, vinyl resin, urea resin, phenol resin, fluorine resin, silicone resin, acrylic resin, melamine resin, epoxy resin, polycarbonate resin, microcrystalline fiber powder, starch powder, lauroyl resin, and the like;

examples of the surfactant metal salt powder include zinc stearate, aluminum stearate, calcium stearate, magnesium stearate, zinc myristate, magnesium myristate, zinc palmitate, zinc laurate, zinc cetyl phosphate, calcium cetyl phosphate, sodium cetyl phosphate, and the like;

examples of colored pigments include inorganic red pigments such as bengara, iron oxide, iron hydroxide, and iron titanate, inorganic brown pigments such as γ-iron oxide, inorganic yellow pigments such as yellow iron oxide, yellow earth, and the like, inorganic black pigments such as black iron oxide, carbon black, and the like, inorganic violet pigments such as manganese violet, cobalt violet, and the like, inorganic green pigments such as chromium hydroxide, chromium oxide, cobalt oxide, cobalt titanate, inorganic blue pigments such as Prussian blue, ultramarine blue and the like, tar based lake dyes such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207, and the like, natural lake pigments such as carminic acid, laccaic acid, carthamin, brazilin, crocin, and the like;

examples of pearl pigments include titanium oxide-coated mica, mica titanium, iron treated mica titanium oxide, titanium oxide-coated mica, bismuth oxychloride, titanium oxide-coated bismuth oxychloride, titanium oxide-coated talc, fish scale flakes, titanium oxide-coated colored mica, and the like; and examples of metal powder pigments include metal powders such as aluminum, gold, silver, copper, platinum, stainless steel, and the like.

A hydrophobic powder is used with the present invention. Therefore, if the surface of the aforementioned powders is not hydrophobic, the surface is preferably hydrophobic treated. Incidentally, these hydrophobic powders may be compounded.

The hydrophobic treatment is not particularly restricted, and treating the powder with any type of hydrophobic surface treating agent can be suggested, and examples include methyl hydrogen polysiloxane (methicone when referred to by the name used in Japanese cosmetic products) treatment, (dimethicone/methicone) copolymer (hydrogen dimethicone when referred to by the name used in Japanese cosmetic products) treatment, dimethyl polysiloxane (dimethicone when referred to by the name used in Japanese cosmetic products) treatment, silicone resin treated, silicone rubber treatment, acrylic silicone treatment, fluorinated silicone treatment, and other organosiloxane treatments; metal soap treatments such as zinc stearate treatments and the like; silane treatments such as silane coupling agent treatments, alkyl silane treatments, and the like; fluorine compound treatments such as perfluoroalkyl silane, perfluoroalkyl phosphate esters, perfluoro polyether treatments, and the like; amino acid treatment such as N-lauroyl-L-lysine treatment; oily agent treatments such as squalane treatment; acrylic treatments such as alkyl acrylate treatments, and the like; and two or more of these may be combined and used together.

Of these treatments, treatment using silicone compounds are preferable from the perspective of water resistance and the ease of dispersing by the carboxylic acid modified silicone, and of these treatments, treatments using methyl hydrogen polysiloxane, (dimethicone/methicone) copolymers, dimethyl polysiloxane, or alkyl silane are particularly preferable.

A silicone elastomer powder can also be used as the hydrophobic powder. The silicone elastomer powder is a cross-linked compound of a straight chain diorganopolysiloxane made primarily from diorganosiloxy units (D units), and can be preferably obtained by causing a cross-linking reaction of an organic hydrogen polysiloxane having a silicon bonded hydrogen atom on a sidechain or terminus, and a diorganopolysiloxane having an unsaturated hydrocarbon group such as an alkenyl group or the like on a sidechain or terminus, in the presence of a hydrosilylating reaction catalyst. The silicone elastomer powder is softer and more elastic than a silicone resin powder made of T units and Q units, can furthermore, the oil absorption is excellent, so oils on the skin can be absorbed to prevent makeup smearing.

The silicone elastomer powder can have various shapes such as spherical, flat, irregular, or the like. The silicone elastomer powder may be in the form of an oil dispersion. A silicone elastomer powder that has a particle form and that has a primary particle diameter when observed using an electron microscope or an average primary particle size when measured by a laser diffraction/diffusion method that is within a range of 0.1 to 50 μm, and where the primary particle shape is spherical can be preferably added to the cosmetic material of the present invention. The silicone elastomer that forms the silicone elastomer powder preferably has a hardness of 80 or less, more preferably 65 or less, when measured by the "vulcanized rubber and thermoplastic rubber hardness test method" in JIS K 6253 using a Type A durometer.

The silicone elastomer powder may be optionally surface treated using a silicone resin, silica, or the like. Examples of the surface treatment include those proposed in Japanese Unexamined Patent Application H2-243612, Japanese Unexamined Patent Application H8-12545, Japanese Unexamined Patent Application H8-12546, Japanese Unexamined Patent Application H8-12524, Japanese Unexamined Patent Application H9-241511, Japanese Unexamined Patent Application H10-36219, Japanese Unexamined Patent Application H11-193331, and Japanese Unexamined Patent Application 2000-281523, and the like. Incidentally, the silicone elastomer powder corresponds to the cross-linked silicone powder mentioned in "Formulation Component Standard by Type of Cosmetic Product". Examples of commercial products of the silicone elastomer powder include Trefil E-506S, Trefil E-508, 9701 Cosmetic Powder, 9702 Powder, and the like, manufactured by Dow Corning Toray Co., Ltd. These silicone elastomer powders can be surface treated, and examples of the surface treatment agent include methyl hydrogen polysiloxane, silicone resin, metal soap, silane coupling agents, silica, inorganic oxides such as titanium oxide, and fluorinated compounds such as perfluoroalkyl silane, perfluoroalkyl phosphate esters, and the like.

Of these hydrophobic powders, fine particle inorganic powders that have been hydrophobic treated are preferable from the perspective of ultraviolet light preventing effects, and of these, hydrophobic fine powder titanium oxide and/or hydrophobic fine particle zinc oxide are preferable. The particle diameter of the hydrophobic fine particle titanium oxide and/or hydrophobic fine powder zinc oxide is preferably 1 to 200 nm, more preferably 10 to 80 nm, from the perspective of dispersibility and the ultraviolet light preventing effect. Furthermore, with the present invention, a hydrophobic treated inorganic pigment powder or pearl pigment powder or the like can be used as the hydrophobic inorganic particles, and the hydrophobic treated fine particle inorganic powder and the hydrophobic treated inorganic pigment powder or the like can be combined and used.

The amount of the hydrophobic powder in the cosmetic material of the present invention is not particularly restricted, but is preferably 1 to 40 mass %, more preferably 2 to 35 mass %, even more preferably 3 to 30 mass %, yet even more preferably 4 to 25 mass %, and still yet even more preferably 5 to 20 mass %, based on the total mass of the cosmetic material.

[Carboxylic Acid Modified Silicone]

The cosmetic material of the present invention contains at least one of (B) carboxylic acid modified silicone.

The carboxylic acid modified silicone in the cosmetic material of the present invention is present in the cosmetic material in a condition where the carboxylic acid modified site is anionized, because of the presence of the basic compound described below. Therefore, the carboxylic acid modified silicone functions as a surfactant or a dispersing agent, and can favorably disperse the (A) hydrophobic powder in the cosmetic material of the present invention.

The carboxylic acid modified silicone that is included in the cosmetic material of the present invention is not particularly restricted, so long as being an organosiloxane where an organic group having at least one carboxyl group is introduced to a sidechain or terminus. Preferably, the organic group having a carboxyl group is introduced to a sidechain of the organo siloxane.

Therefore, the carboxylic acid modified silicone can be a compound where an organic group having a carboxyl group is grafted onto a silicone main chain, a compound where an organic group having a carboxyl group is added to one and of a silicone main chain, a compound where the organic group having a carboxyl group is added to both ends of a silicone main chain, compounds where the organic group having a carboxyl group is added to both ends of the silicone main chain, and an organic group having a carboxyl group is also grafted, compounds where an organic group having a carboxyl group and a silicone group (including a siloxane macro monomer bonded by a silalkylene bond) is grafted, compounds with a siloxane modified group having a carbosiloxane dendolimer structure and an organic group having a carboxyl group on the silicone main chain or terminus, and compounds that also optionally have a long chain alkyl group with 6 or more carbon atoms. Most preferable are compounds where an organic group having a carboxyl group is grafted onto the silicone main chain. Incidentally, the formulation stability with an organic oily agent such as a hydrocarbon oil or the like, or an organic cosmetic raw material (in particular, a UV absorber) may be enhanced if the carboxylic acid modified silicone has a long chain alkyl group.

A linking group may be present between the carboxyl group and the silicone atom, and examples of the linking group include an alkylene group which may also have a heteroatom, or a bivalent or higher organic group such as a polyoxyalkylene group or the like, but there is no restriction to these. Furthermore, a carboxylic acid modified silicone where (n–1) carboxyl groups are bonded to the silicone atom using a linking group with a valence of n (n is an integer 3 or higher) can be used. Specifically, a silicone having a carboxyl group on the silicone main chain or sidechain through the following linking groups are included in the carboxylic acid modified silicone of the present invention.

Examples include the following organopolysiloxane with an organic group having a carboxyl group bonded to the silicon atom described in Japanese PCT Patent Application H11-504665:

[Formula 2]

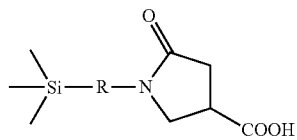

(Where R represents a bivalent group including a $C_1$-$C_{12}$ alkylene group, $C_1$-$C_{12}$ alkyleneoxy group, an oxygen atom, a sulfur atom, —NH—, —NR'— (R' represents a $C_1$-$C_6$ alkyl group), or a combination thereof), any one of the following organopolysiloxane having an organic group described in Japanese Unexamined Patent Application 2002-114849:

[Formula 3]

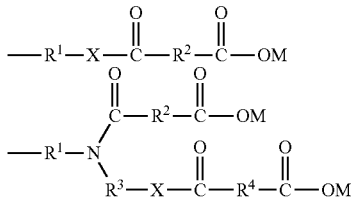

(Where $R^1$ to $R^4$ represent the same or different substitution group having a heteroatom, straight chain or branched alkylene group, alkenylene, or arylene group with 2 to 22 carbon atoms, X represents —O—, or NH—, and M represents a hydrogen atom), the following organopolysiloxane with an organic group having a carboxyl group as described in Japanese PCT Patent Application H2005-524747:

[Formula 4]

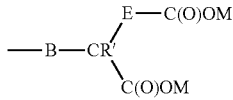

(Where, B represents an alkylene residual group with 20 to 30 carbon atoms and which may optionally be substituted by one or more alkyl group with 1 to 30 carbon atoms, R' represents a hydrogen atom or an alkyl group with 1 to 30 carbon atoms, E either does not exist, or is an alkylene residual group with 1 to 5 carbon atoms, preferably 1 to 3 carbon atoms, which may optionally be substituted with one or more alkyl group having 1 to 30 carbon atoms; M represents a hydrogen atom), the following organopolysiloxane with an organic group having a carboxyl group expressed by the following average composition formula as described in Japanese Unexamined Patent Application 2009-263643:

[Formula 5]

$$R^1_a R^2_b R^3_c SiO_{(4-a-b-c)/2} \quad (1)$$

[Where, $R^1$ is a group selected from alkyl groups with 1 to 30 carbon atoms, fluoroalkyl groups with 1 to 30 carbon atoms, aryl groups with 6 to 30 carbon atoms, and aralkyl groups with 6 to 30 carbon atoms, $R^2$ is a group expressed by the following formula (2) where if c is 0, $R^2$ is bonded to at least one terminus of the organopolysiloxane,

[Formula 6]

(Where $R^4$ is a bivalent hydrocarbon group with 2 to 20 carbon atoms and which may or may not have an oxygen atom, $R^5$ is a hydrogen atom, $R^6$ are mutually independent and can be a hydrogen atom or an alkyl group with 1 to 6 carbon atoms, and $R^7$ is a hydrogen atom or an alkyl group with 1 to 6 carbon atoms)

$R^3$ represents a group expressed by the following formula (3)

[Formula 7]

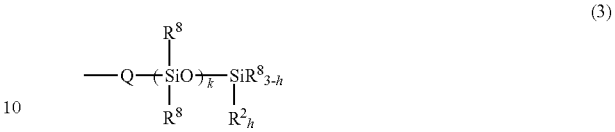

(where $R^2$ is as described above, $R^8$ are mutually independent, and are groups selected from alkyl groups with 1 to 30 carbon atoms, fluoroalkyl groups with 1 to 30 carbon atoms, aryl groups with 6 to 30 carbon atoms, and aralkyl groups with 6 to 30 carbon atoms, Q represents $C_d H_{2d}$ (where d is an integer of 1 to 5, preferably an integer of 2 to 4) or an oxygen atom, k is an integer from 0 to 500, preferably 1 to 100, and more preferably 5 to 60, and h is an integer of 0 to 3, preferably 0).

The carboxylic acid modified silicone that is used in the present invention is particularly preferably a silicone where at least one silicon atom on a sidechain or terminus of the silicone main chain is bonded to an organic group with a carboxyl group expressed by the general formula: —$R^1$—$(OR^2)$p-(O)w-$R^3$—COOH (where $R^1$ represents a straight chain or branched alkylene group with 2 to 22 carbon atoms; $R^2$ represents a straight chain or branched alkylene group with 2 to 4 carbon atoms; $R^3$ represents a bond (—) or a straight chain or branched alkylene group with 1 to 22 carbon atoms; p represents a number between 0 and 200; and w represents a number of 0 or 1).

In the general formula that expresses the organic group having a carboxyl group, $R^1$ represents a straight chain or branched alkylene group with 2 to 22 carbon atoms, preferably 2 to 12 carbon atoms, and particularly preferably 2 to 10 carbon atoms, and specific examples include ethylene, propylene, trimethylene, butylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene group and the like.

Furthermore, examples of the straight chain or branched alkylene group with 2 to 4 carbon atoms as $R^2$ include ethylene, propylene, trimethylene, and butylene groups, but an ethylene group is particularly preferable.

Examples of the straight chain or branched alkylene group with 1 to 22 carbon atoms as $R^3$ include methylene, ethylene, ethyl ethylene, propylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, and the like, and of these, those with 1 to 12 carbon atoms are preferable, and particularly preferably those where the sum of the carbon atoms of $R^1$ and $R^3$ is 2 to 22.

p represents an integer between 0 and 200, but is preferably an integer between 0 and 20, particularly preferably an integer between 0 and 10. Furthermore, w represents an integer of 0 or 1, but is preferably 0. Incidentally, if both p and w are 0, the organic group having a carboxyl group will be expressed by the structural formula —$(C_n H_{2n})$—COOH, and preferably has a structure where it the one carboxyl group is bonded to a silicone atom through a straight chain or branched alkylene group with 3 to 44 carbon atoms. Incidentally, in the formula, n represents a number from 3 to 44, preferably a number from 3 to 20, and particularly preferably a number from 3 to 16.

The carboxylic acid modified silicone that is used in the present invention can be an organopolysiloxane expressed by the structural formula (A):

[Formula 8]

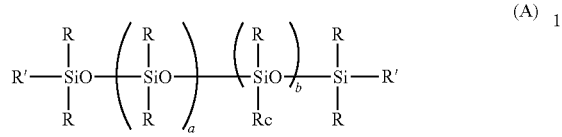

(A)

(In the formula, Rc represents an organic group containing a carboxyl group expressed by the general formula: —$R^1$—($OR^2$)p-(O)w-$R^3$—COOH, where R can be the same or different, and represents an alkyl group or alkoxy group having 1 to 22 carbon atoms, or phenyl group, R' represents Rc or R, a and b are both integers that are 0 or higher, and a+b is an integer within a range of 0 to 1000, with the proviso that when b=0, at least one of R' is Rc). In particular, the carboxylic acid modified silicone disclosed in Japanese Unexamined Patent Application H8-109263 and a portion of the carboxylic acid modified silicone disclosed in International Unexamined Patent Application 2009/22621 (other than those having a siloxane dendron structure) are included in the carboxylic acid modified silicones that are preferably used in the present invention and that are expressed by the structural formula (A).

Examples of a more preferable carboxylic acid modified silicone expressed by structural formula (A) include a carboxylic acid modified silicone where an organic group having a carboxyl group expressed by the general formula: —$R^1$—($OR^2$)p-(O)w-$R^3$—COOH is grafted onto the silicone main chain and a+b is an integer within a range of 0 to 500, and b>0, and a carboxylic acid modified silicone where an organic group having a carboxyl group where R' on both ends of the silicone chain or expressed by the general formula: —$R^1$—($OR^2$)p-(O)w-$R^3$—COOH, and b=0. With the present invention, a particularly preferable carboxylic acid modified silicone has an organic group with a plurality of carboxyl groups on a sidechain portion, preferably b>a, and more preferably b>0 and a=0. b>a means that more than half of the siloxane units of the side chain part have an organic group having a carboxyl group, and preferably, a+b is an integer within a range of 1 to 500. Furthermore, when a=0 and b>0, the siloxane units of the sidechain portion all have an organic group with a carboxyl group, and most preferably, b is a number within a range of 1 to 200, preferably a number within a range of 1 to 50.

In structural formula (A), R preferably represents a methyl group, alkoxy group, or phenyl group, but at least a portion have a long chain alkyl group with 6 to 22 carbon atoms, from the perspective of formulation stability with the organic cosmetic material raw materials (in particular, UV absorbers) and organic-based oily agents such as hydrocarbon oils and the like. The conversion rate of the organic groups having a carboxyl group is not particularly restricted, but if a+b is within a range of 0 to 500, the number of organic groups having a carboxyl group is preferably 2 to 100 on average in the molecule, including the case where an organic group having a carboxyl group is bonded to both ends of the silicone main chain.

With the present invention, the carboxylic acid modified silicone can be produced by a commonly known method, for example, a method of causing an addition reaction between the dimethyl polysiloxane having an Si—H group and the unsaturated carboxylic acid ester compound in the presence of a platinum catalyst; a method of obtaining the target by causing an addition reaction of a dimethyl polysiloxane having a Si—H group and an unsaturated carboxylic acid sylyl ester or aryloxy carboxylic acid sylyl ester in the presence of a platinum catalyst, and then hydrolyzing; and a method of obtaining a silicone modified with carboxylic acid on both ends by causing an equilibrium reaction using bis(hydroxycarbonyl ether), tetramethyldisiloxane, and acyclic siloxane using an acidic catalyst, to obtain a silicone modified with carboxylic acid on both ends (Silicone Handbook, Ito Kunio, ed., Nikkan Kogyo Shimbun, pp. 166 to 167), and the like.

Furthermore, in the present invention, commercial products of the carboxylic acid modified silicone can be used as is, or after removing the solvent, and specific examples include SF8418, BY16-880, BY16-754, BY16-750, FV20-56, FZ-3806 (manufactured by Dow Corning Toray Co., Ltd.), TSF4770, TSF4771 (Momentive Performance Materials Co. Ltd.), X-22-162A, X-22-162C, X-22-3701E, X-22-3710 (Shin-Etsu Chemical Co., Ltd.) and the like.

The cosmetic of the present invention preferably contains the (B) carboxylic acid modified silicone within a range of 0.01 to 20 mass parts with regard to 10 mass parts of the hydrophobic powder, more preferably within a range of 0.1 to 15 mass parts, and even more preferably within a range of 1 to 10 mass parts.

[Basic Compound]

The cosmetic material of the present invention contains at least one of (C) basic compound.

The basic compound that is used in the present invention is not particularly restricted so long as being a compound that demonstrates basicity when dissolved in water, and any type of inorganic compound or organic compound can be used. One or more of basic compound can be added.

Examples of the organic compounds include mono ethanolamine, triethanolamine, 2-amino-2-methyl-1,3-propanol, amino methyl propanol, arginine, guanidine, and the like.

Examples of the inorganic compound include sodium hydroxide, sodium carbonate, potassium hydroxide, potassium carbonate, calcium hydroxide, calcium carbonate, ammonia, and the like, but of these, potassium hydroxide is particularly preferably used.

The amount of the basic compound in the cosmetic material of the present invention is not particularly restricted, but for the case of a monovalent base with regard to 1 mole of the carboxylic acid group that is included in the carboxylic acid modified silicone that is added, the ratio of carboxylic acid groups/monovalent base (mole ratio) is preferably 1/0.5 to 1/1.5. Specifically, 0.01 to 5 mass % is preferable, 0.03 to 4 mass % is more preferable, 0.05 to 4 mass % is even more preferable, and 0.08 to 3 mass % is yet even more preferable, using the total mass of the cosmetic material as a basis.

[Water]

The cosmetic material of the present invention includes (D) water. The water forms an aqueous phase in the cosmetic material of the present invention.

The amount of the water in the cosmetic material of the present invention is not particularly restricted, but is preferably 20 to 95 mass %, more preferably 40 to 80 mass %, even more preferably 45 to 70 mass %, yet even more preferably 47 to 65 mass %, and still yet even more preferably 50 to 60 mass %, based on the total mass of the cosmetic material.

The pH of the cosmetic material of the present invention is preferably a week alkaline, and specifically, a range of 7.1 to 9.5 is preferable, and a range of 7.2 to 8.5 is more preferable.

If the pH of the cosmetic material of the present invention is alkaline, the (B) carboxylic acid modified silicone can favorably demonstrate a function as a surfactant, because the carboxylic acid modified sites of the (B) carboxylic acid modified silicone will be anionized. Therefore, the (A) hydrophobic powder will be favorably dispersed in the aqueous phase, and can be maintained in a stable dispersed condition over time.

[Polyhydric Alcohol]

The cosmetic material of the present invention can include at least one of (G) polyhydric alcohol.

By adding the polyhydric alcohol, the moisture retaining feel and the feel of use of the cosmetic material of the present invention can be adjusted, and the hydrophobic powder of component (A) can be more uniformly dispersed in the aqueous phase by blending with beforehand with the polyhydric alcohol.

Examples of the polyhydric alcohol include sorbitol, xylitol propylene glycol, dipropylene glycol, 1,3-butylene glycol, glycerin, diglycerin, polyethylene glycol, and the like, and these polyhydric alcohols can be used individually, or two or more can be combined and used together. If component (B) and the hydrophobic powder of component (A) or mixed together beforehand, the polyhydric alcohol is preferably propylene glycol, dipropylene glycol, 1,3-butylene glycol, glycerin, diglycerin, and combinations thereof.

The amount of the polyhydric alcohol in the cosmetic material of the present invention is not particularly restricted, but is preferably 0.3 to 30 mass %, more preferably 0.5 to 25 mass %, even more preferably 1 to 20 mass %, yet even more preferably 2 to 20 mass %, and still yet even more preferably 3 to 15 mass %, based on the total mass of the cosmetic material.

[Oily Agent]

The cosmetic material of the present invention can include at least one of (E) oily agent.

The "oily agent" of the present invention is generally used as a component of the cosmetic material, and is not particularly restricted. The oily agent is normally a liquid at room temperature, but can also be a solid such as a wax, and can also have a high viscosity and be in the form of a viscous rubber or paste, as described below.

The oily agent is preferably at least one that is a liquid at a temperature between 5 and 100° C., selected from the group consisting of silicone oils, nonpolar organic compounds, and low polarity organic compounds.

Silicone oils are hydrophobic, and the molecular structure can be cyclic, straight chain, or branched. The viscosity of the silicone oil at 25° C. is normally in a range of 0.65 to 100,000 mm$^2$/s, preferably within a range of 0.65 to 10,000 mm$^2$/s.

Examples of the silicone oil include straight chain organopolysiloxane, cyclic organopolysiloxane, and branched organopolysiloxane. Of these, volatile straight chain organopolysiloxane, cyclic organopolysiloxane, and branched organopolysiloxane are preferable.

More specifically, examples of straight chain organopolysiloxanes include dimethyl polysiloxane blocked on both ends of the molecular chain by a trimethyl siloxane group (dimethyl silicone with a low viscosity of 2 mPa·s or 6 mPa·s, to a high viscosity of 1,000,000 mPa·s, and the like), organohydrogenpolysiloxane with both molecular chain terminals blocked by trimethylsiloxy groups, methylphenyl polysiloxane with both molecular chain terminals blocked with trimethylsiloxy groups, dimethylsiloxane-methylphenylsiloxane copolymers with both molecular terminals blocked with trimethylsiloxy groups, diphenylpolysiloxanes with both molecular chain terminals blocked with trimethylsiloxy groups, dimethylsiloxane-diphenylsiloxane copolymer, trimethyl pentaphenyl trisiloxane, phenyl (trimethylsiloxy) siloxane with both molecular chain terminals blocked by trimethylsiloxy groups, methyl alkyl polysiloxane with both molecular terminals blocked with trimethylsiloxy group, dimethylpolysiloxane-methyl alkyl siloxane copolymer with both molecular terminals blocked with trimethylsiloxy groups, dimethylsiloxane-methyl (3,3,3-trifluoropropyl) siloxane copolymer, α, ω-dihydroxy polydimethylsiloxane, α, ω-diethoxycarboxymethyl polydimethylsiloxane, 1,1,1,3,5,5,5 heptamethyl-3-octyl trisiloxane, 1,1,1,3,5,5,5 heptamethyl-3-dodecyltrisiloxane, 1,1,1,3,5,5,5 heptamethyl-3-hexadecyltrimethyl ammonium siloxane, tristrimethylsiloxymethylsilane, tris trimethylsiloxy alkyl silane, tetrakis trimethylsiloxy silane, tetramethyl-1,3-dihydroxy disiloxane, octamethyl-1,7-dihydroxy tetrasiloxane, hexamethyl-1,5-diethoxycarboxymethyl trisiloxane, hexamethyldisiloxane, octamethyltrisiloxane, higher alkoxy-modified silicone, higher fatty acid-modified silicone, dimethiconol, and the like.

Examples of the cyclic organopolysiloxane include hexamethylcyclotrisiloxane (D3), octamethylcyclotetrasiloxane (D4), decamethylcyclopentasiloxane (D 5), dodecamethylcyclohexasiloxane (D6), 1,1-diethylhexamethyl cyclotetrasiloxane, phenylalanine heptamethylcyclotetrasiloxane, 1,1-diphenyl hexamethyl cyclotetrasiloxane, 1,3,5,7 tetravinyltetramethylcyclotetrasiloxane, 1,3,5,7-tetra methyl cyclotetrasiloxane, 1,3,5,7-tetra-cyclohexyl tetramethylcyclotetrasiloxane, tris (3,3,3-trifluoropropyl) trimethylcyclotrisiloxane, 1,3,5,7-tetra (3-methacryloxypropyl) tetramethyl cyclotetrasiloxane, 1,3,5,7-tetra (3-acryloxypropyl) tetramethyl cyclotetrasiloxane, 1,3,5,7-tetra (3-carboxypropyl) tetramethyldisiloxane cyclo tetrasiloxane, 1,3,5,7-tetra (3 vinyloxy propyl) tetramethylcyclotetrasiloxane, 1,3,5,7-tetra (p-vinyl phenyl) tetramethylcyclotetrasiloxane, 1,3,5,7-tetra [3-(p-vinylphenyl) propyl] tetramethylcyclotetrasiloxane, 1,3,5,7-tetra (N-acryloyl-N-methyl-3-aminopropyl) tetramethyl cyclotetrasiloxane, 1,3,5,7-tetra (N,N-bis (laurayl)-3-aminopropyl) tetramethyl cyclotetrasiloxane, and the like.

Examples of the branched organopolysiloxane include methyl tris trimethylsiloxy silane, ethyl tris trimethylsiloxy silane, propyl tris trimethylsiloxy silane, tetrakis trimethylsiloxy silane, phenyl tris trimethylsiloxy silane, and the like.

The nonpolar organic compound or low polarity organic compound is preferably a hydrocarbon oil or a fatty acid ester oil. These are components that are particularly widely used as a base material for makeup cosmetic materials.

Examples of hydrocarbon oils include liquid paraffin, light liquid isoparaffin, heavy liquid isoparaffin, vaseline, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene polypropylene wax, squalane, squalene, pristane, polyisoprene, and the like.

Examples of the fatty acid ester oils include hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, propylene glycol dioleate, glyceryl tri-2-ethylhexanoate, trimethylolpropane tri-2-ethylhexanoate, ditrimethylolpropane triethylhexanoate, ditrimethylolpropane triethylhexanoate, ditrimethylolpropane (isostearate/sebacate), trimethylolpropane trioctanoate, trimethylolpropane triisostearate, diisopropyl adipatae, diisobutyl adipate, 2-hexyl decyl adipate, di-2-heptylundecyl adipate, diisostearyl malate, hydrogenated castor oil monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentyl glycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyl octyl sebacate, cetyl palmitate, octyldodecyl palmitate, octyl palmitate, 2-ethylhexyl palmitate, 2-hexyl decyl palmitate, 2-heptyl undecyl palmitate, cholesteryl 12-hydroxy stearate, dipentaerythritol fatty acid ester, 2-hexyl decyl myristate, ethyl laurate, 2-octyl-dodecyl N-lauroyl-L-glutamate ester, di (cholesteryl/behenyl/octyldodecyl) N-lauroyl-L-glutamate, di(cholesteryl/octyldodecyl) N-lauroyl-L-glutamate, di (phytosteryl/behenyl/octyldodecyl) N-lauroyl-L-glutamate, di (phytosteryl/octyldodecyl) N-lauroyl-L-glutamate, isopropyl N-lauroyl sarcosine, diisostearyl maleate, neopentyl glycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethyl pentanediol dineopentanoate, methyl pentanediol dineopentanoate, octyldodecyl neodecanoate, 2-butyl-2-ethyl-1,3-propanediol dioctanoate, pentaerythrityl tetraoctanoate, pentaerythrityl hydrogenated rosin, pentaerythrityl triethyl hexaoate, dipentaerythrityl (hydroxystearate/stearate/rosin acid ester), polyglyceryl tetraisostearate, polyglyceryl 10 nonaisostearate, polyglyceryl 8 deca (erucate/isostearate/ricinoleate), diglyceryl (hexyldecanoate/sebacate) oligo ester, glycol (distearate ethylene glycol) distearate, diisopropyl dimer linoleate, diisostearyl dimer linoleate, di(isostearyl/phytosteryl)dimer linoleate, (phytosteryl/behenyl) dimer linoleate, (phytosteryl/isostearyl/cetyl/stearyl/behenyl) dimer linoleate, dimer dilinoleyl dimer dilinoleate, dimer lenoleyl diisostearate, dimer lenoleyl hydrogenated rosin condensate, hydrogenated castor oil dimer linoleate, hydroxyalkyl dimer linoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri (caprylate/caprate), glyceryl tri (caprylate/caprate/myristate/stearate), hydrogenated rosin triglyceride (hydrogenated ester gum), rosin triglyceride (ester gum), glyceryl behenate eikosanoate, glyceryl di-2-heptyl undecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl macadamia nut oil fatty acid ester, phytosteryl macadamia nut oil fatty acid ester, phytosteryl isostearate, cholesteryl soft lanolin fatty acid ester, cholesteryl hard lanolin fatty acid ester, cholesteryl long-chain branched fatty acid ester, cholesteryl long-chain α-hydroxy fatty acid ester, octyldodecyl ricinoleate, octyldodecyl lanolin fatty acid ester, octyldodecyl erucate, hydrogenated castor oil isostearate, ethyl avocado oil fatty acid ester, isopropyl lanolate, and the like.

The low polarity organic compound can be a higher alcohol with 10 to 30 carbon atoms, for example. If a higher alcohol is used as an emulsification stabilizing component, the amount of hydrophilic surfactant can be reduced, and the water resistance can be further enhanced. The higher alcohol is a saturated or unsaturated mono hit Drake aliphatic alcohol, and the hydrocarbon group portion can be either straight chain or branched, but straight chain is more preferable. Examples of higher alcohols with 10 to 30 carbon atoms include lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyltetradecinol, cholesterol, sito sterol, phytostearol, lanostearol, lanolin alcohol, hydrogenated lanolin alcohol, and the like. Note, with the present invention, a higher alcohol with a melting point of 40 to 80° C. can be used individually, or a combination of a plurality of higher alcohols where the melting point is 40 to 70° C. is preferable.

The amount of the oily agent in the cosmetic material of the present invention is not particularly restricted, but is preferably 3 to 60 mass %, more preferably 4 to 50 mass %, even more preferably 5 to 40 mass %, yet even more preferably 6 to 30 mass %, and still yet even more preferably 7 to 20 mass %, based on the total mass of the cosmetic material.

[Salt of a Higher Fatty Acid]

The cosmetic material of the present invention can include at least one of (F) salt of a higher fatty acid.

The salt of the higher fatty acid can be used as an emulsifying agent. The higher fatty acid component that is used to form the salt can be simply configured as a liquid higher fatty acid, or can be configured as a mixture of a liquid higher fatty acid and a solid higher fatty acid, but a liquid higher fatty acid is preferably included. If only a solid higher fatty acid is used, the stretching and spreading properties will be insufficient, and the grime that is washed off by the soap will be reduced. The ratio of liquid higher fatty acid is preferably at least 30 mass % or more, more preferably 50 mass % or more, even more preferably 90 mass % or more, of the total mass of the higher fatty acid, and the stretching and spreading properties will be improved as this ratio increases, and the cleaning properties of the soap will be enhanced. Furthermore, if the higher fatty acid component contains only liquid higher fatty acids, there are economic benefits because there will not be a need to provide a step of heating when producing the cosmetic material, and the quality of the cosmetic material will be stable.

The type of higher fatty acid is not particularly restricted, and examples include saturated fatty acids and unsaturated fatty acids, such as lauric acid, myristic acid, palmitic acid, stearic acid, behenic acid, undecylenic acid, oleic acid, linoleic acid, linolenic acid, arachidonic acid, eicosapentaenoic acid (EPA), hexyldecanoic acid, docosahexaenoic acid (DHA), isostearic acid, and the like, but fatty acids with 9 to 26 carbon atoms are preferable, and those with 11 to 22 carbon atoms are more preferable. These may be used independently, or two or more may be used in conjunction.

Of these, the liquid fatty acids isostearic acid, hexyldecanoic acid, and oleic acid are preferable, and isostearic acid is more preferable.

With the present invention, isostearic acid refers to a mixture of one or more of branched stearic acid. For example, 5,7,7,-trimethyl-2-(1,3,3-trimethyl butyl) octanoic acid can be produced by making a branched aldehyde with 9 carbon atoms by an oxo reaction of an iso-butylene dimer, forming a branched unsaturated aldehyde with 18 carbon atoms by performing Aldol condensation of this aldehyde, and then performing a hydrogenation reaction and an oxidation reaction (hereinafter referred to as the "Aldol condensation type"). Isostearic acid from aldol condensation is commercialized by Nissan Chemical Industries. Furthermore, 2-heptyl undecanoic acid can be produced by dimerizing nonyl alcohol using the Guerbet reaction, and then oxidizing. 2 heptyl undecanoic acid has been commercialized by Mitsubishi Chemicals, and a similar compound with a slightly different branched position is commercialized by Nissan Chemical Industries. Furthermore, Nissan Chemical Industries has also commercialized a type where the starting alcohol is not a straight chain alcohol, but is branched in 2 locations (hereinafter these are generally referred to as the "Guerbet reaction type").

Furthermore, isostearic acid that is called Emery type can also be used. Emery type isostearic acid can be obtained by hydrogenating unsaturated fatty acid which is a byproduct when synthesizing dimer acid from oleic acid, has 18 carbon atoms with a methyl group on a sidechain, and the structure is unclear (for example, refer to J. Amer. Oil Chem. Soc. 51, 522 (1974)), and specific examples include the isostearic acid sold by US based Emery and the isostearic acid EX produced by Higher Alcohol Industries. The starting substance for the dimer acid which is set starting substance for the Emery type isostearic acid may contain not only oleic acid, but also linoleic acid and linolenic acid, and the like. With the present invention, the Emery type is preferably used.

With the present invention, the solid higher fatty acid that can be used in combination with the liquid higher fatty acid normally has 10 to 25 carbon atoms, preferably 11 to 22 carbon atoms, and specific examples include stearic acid, behenic acid, hydroxy stearic acid, palmitic acid, myristic acid, and lauric acid.

The aforementioned higher fatty acids may be used as a salt of the higher fatty acid by first neutralizing using a base, but in the manufacturing process of the cosmetic material of the present invention, (C) a basic compound is also added to the higher fatty acid, so a higher fatty acid salt can be formed by neutralizing both components in the manufacturing process. If both components are added separately, the higher fatty acid component and the basic compound are normally added in the equivalent amounts, but equivalent amounts is not necessarily mandatory, and the amount of bowls can be adjusted such that the pH of the aqueous phase of the cosmetic material produced is within a range of 7.1 to 9.5, and for example, appropriate production is possible if the higher fatty acid/basic compound (mole ratio) is within a range of 1/0.5 to 1/1.5.

The amount of the higher fatty acid salt in the cosmetic material of the present invention is not particularly restricted, but is preferably 0.1 to 12 mass %, more preferably 0.5 to 10 mass %, and even more preferably 1 to 5 mass %.

[Water-Soluble Thickening Agent]

The cosmetic material of the present invention can include at least one of (H) water-soluble thickening agent.

The viscosity and the feel of use of the cosmetic material of the present invention can be adjusted, and the storage stability can be further enhanced by the adding a water-soluble thickening agent.

Examples of the water-soluble thickening agent include carboxyvinyl polymers, sodium polyacrylate, polyethylene glycol, copolymer of acrylic acid and alkyl methacrylate polyoxyethylene polyoxypropylene block copolymer, polyvinyl alcohol, polyvinyl pyrrolidone, polyvinyl methyl ether, methyl cellulose, ethyl cellulose, hydroxyethyl cellulose, hydroxypropyl cellulose, hydroxypropyl methyl cellulose, cationized cellulose, sodium alginate, propylene glycol alginate, guar gum, locust bean gum, carrageenan, xanthan gum, dextran, bentonite, and the like, preferably, carboxyvinyl polymers, acrylic and alkyl methacrylate copolymer, polyvinyl alcohol, polyvinyl pyrrolidone, and hydroxypropyl methylcellulose. These water-soluble thickening agents can be used individually, or two or more can be combined.

The amount of the water-soluble thickening agent in the cosmetic material of the present invention is not particularly restricted, but is preferably 0.01 to 3 mass %, more preferably 0.05 to 2 mass %, even more preferably 0.1 to 2 mass %, yet even more preferably 0.3 to 1.5 mass %, and still yet even more preferably 0.5 to 1 mass %, based on the total mass of the cosmetic material.

[Optional Components]

The cosmetic material of the present invention can also contain other components that are normally used in cosmetic materials, within a range that the effect of the present invention is not hinder, and examples include ultraviolet absorbers, organic resins, hydrophilic powders, moisturizers other than component (G), thickening agent other than component (H), preservatives, antimicrobial agents, perfumes, salts, antioxidants, pH adjusting agents other than component (C), chelating agents, refreshing agents, anti-inflammatory agents, physiologically active ingredient (whitening agents, cell activators, skin roughness-improving agents, blood circulation promoters, skin astringents, antiseborrheic agents), vitamins, amino acids, nucleic acids, hormones, clathrates, and the like. These components are not particularly restricted.

[Manufacturing Method]

The manufacturing process of the cosmetic material of the present invention is optional, and is not particularly restricted so long as the cosmetic material can be made by blending the (A) hydrophobic powder, (B) carboxylic acid modified silicone, the C basic compound, and (D) water, and the (A) hydrophobic powder can be dispersed in the aqueous phase.

The cosmetic material of the present invention can be produced by a step of producing an aqueous dispersion where component (A) is dispersed in the aqueous phase by mixing the components (A) to (D). If necessary, at least one of component selected from the group consisting of components (E), (F), (G), and (H) can be added.

The manufacturing method of the cosmetic material of the present invention preferably includes a step of dispersing in an aqueous phase a mixture containing at least component (A) and component (B).

The pH of the aqueous dispersion is preferably within a range of 6.5 to 14.0, more preferably within a range of 7.0 to 12.0, and even more preferably within a range of 7.5 to 10.0.

Component (G) is preferably a mixed together with components (A) to (D), from the perspective of dispersibility of the hydrophobic powder in the aqueous phase.

For example, the manufacturing method of the cosmetic material of the present invention preferably includes a step of first mixing the (G) polyhydric alcohol, (A) hydrophobic powder, and (B) carboxylic acid modified silicone (a slurry composition as a precursor), and more preferably includes a step of producing an aqueous dispersion where the hydrophobic powder is dispersed in an aqueous phase with the pH of 6.5 to 14.0 by blending the (C) basic compound and the (D) water with a mixture that contains components (A), (B), and (G) that was obtained by a preliminary mixing step.

The initial dispersibility of the (A) hydrophobic powder in the aqueous phase is improved by the step of first mixing the (G) polyhydric alcohol, (A) hydrophobic powder, and (B) carboxylic acid modified silicone. Furthermore, a composition where the (A) hydrophobic powder is dispersed in the aqueous phase (aqueous dispersion) that includes the mixture obtained by the preliminary mixing step can be adjusted to a pH of 6.5 to 14.0 by using component (C) or the like, thereby achieving the advantage of improving the long-term storage stability of the (A) hydrophobic powder in the aqueous phase. The composition can be used as a cosmetic material itself, or can be used as a precursor of the cosmetic material (premixed or cosmetic material raw material) to produce a different cosmetic material.

On the other hand, a cosmetic material where the hydrophobic powder is dispersed in the aqueous phase can also be produced using as the cosmetic material raw materials a mixture that contains (A) hydrophobic powder, (B) carboxylic acid modified silicone, (C) basic compound, and (D) water, without containing (G) a polyhydric alcohol (a slurry composition as a precursor or the like).

Furthermore, a composition (aqueous dispersion) obtained by a step of producing an aqueous dispersion where the (A) hydrophobic powder is dispersed in the aqueous phase and preferably with a pH of 6.5 to 14.0, by mixing the (A) hydrophobic powder, (B) carboxylic acid modified silicone, (C) basic compound, and (D) water, can be used as a cosmetic material itself, or can be used as a precursor of a cosmetic material (premixed or cosmetic material raw material) for producing a different cosmetic material.

If the cosmetic material of the present invention contains component (F), the higher fatty acid which is the raw material of component (F) and the (C) basic compound can be separately in the manufacturing step of the cosmetic material, but reducing a salt of the higher fatty acid is preferable from the perspective of operability and quality stability. Furthermore, if only a liquid higher fatty acid is used as the raw material for component (F), the step of heating which is required when a solid higher fatty acid is used can be omitted, and this has economic advantages while contributing to the stability of the quality.

[Method of Use]

The cosmetic material of the present invention can be used in any form, such as a cream, gel, emulsion, or liquid, and the cosmetic material of the present invention can be used as a base cosmetic material such as an emulsion, cream, or beautifying liquid, as a base layer cosmetic material, as a sunscreen agent, or as a makeup cosmetic materials such as foundation, eye shadow, eyeliner, or water phase powder, or can also be used as a sunscreen agent for the hair and face, or as a temporary hair dying agent, or the like.

If the cosmetic material of the present invention is used as a precursor for a different cosmetic material (premixed or cosmetic material raw material), hydrophobic fine particle inorganic powder can be used as the (A) hydrophobic powder.

The cosmetic material of the present invention preferably is in the form of an oil in water emulsion composition. For the case of an oil in water emulsion, the water that forms the continuous phase will be in direct contact with the skin, so a moist refreshing feel of use can be more strongly provided. Furthermore, the oil in water emulsion composition of the present invention can provide excellent appearance as a cosmetic material with the hydrophobic powder stably dispersed in formulations that were conventionally difficult to design using a hydrophobic powder because of the relationship to dispersibility, and when this oil in water emulsion composition is applied to the skin, excellent water repelling and water resistant properties are achieved because of the hydrophobic powder, and a cosmetic material with excellent application life (long-lasting) can be provided.

The cosmetic material of the present invention is preferably applied to weakly acidic skin, and for example, is preferably applied to skin with a pH of 5.1 to 7.0.

Furthermore, if the amount of cosmetic material of the present invention applied to the skin is 0.5 mg/cm$^2$, the pH of the application surface after 30 min. is preferably 7.0 or less, and more preferably 6.7 or less.

When the cosmetic material of the present invention is applied to the skin, the carboxylic acid modified site of the carboxylic acid modified silicone will be non-ionized by the weak acidity inherent to the surface of the skin, the surfactant performance will drop, and the dispersing function of the hydrophobic powder will be reduced. Therefore, the hydrophobic powder cannot be stably dispersed in the aqueous phase, and will be promptly deposited on the skin. Therefore, a hydrophobic cosmetic film will be formed on the skin.

If the cosmetic material of the present invention contains an oily agent, the oily agent will also be deposited on the skin with the hydrophobic powder when the cosmetic material of the present invention is applied to the skin, and will form a hydrophobic film. The cosmetic film contains an oily agent as well as the hydrophobic powder, and therefore higher water resistance and adhesion can be achieved.

If the cosmetic material of the present invention contains a salt of a higher fatty acid, the dispersion of the hydrophobic powder in the aqueous phase can be more favorably achieved, in addition to the surfactant effect of the carboxylic acid modified silicone, due to the surfactant effect of the salt before applying to the skin. Furthermore, if an oily agent is included, the salt of the higher fatty acid will function as a favorable emulsifying agent, but when applied to the skin, the salt will convert to a free higher fatty acid, and will be deposited on the skin together with the hydrophobic powder and the higher fatty acid, thus forming a hydrophobic cosmetic film. The cosmetic film not only contains hydrophobic powder, but also contains the higher fatty acid (and possibly the oily agent), and therefore higher water resistance can be achieved.

In this manner, the cosmetic material of the present invention can form a cosmetic film with excellent water resistance on the skin, and therefore the cosmetic life will be excellent, and cosmetic smearing due to sweat, rain, or the like will not easily occur.

EXAMPLES

The present invention will be described below in further detail based on examples, but the present invention is not restricted to these embodiments. The formulation amounts of each component are expressed as "mass %" ("weight %") unless otherwise expressly noted.

Reference Example 2.5 g of isostearic acid and 0.02 g of potassium hydroxide were dissolved in 100 g of purified water to produce a potassium isostearate solution with a pH of 7.9, and then 0.5 mg/cm$^2$ was applied using a finger to which a rubber sack was attached onto the inside forearm of female panelists (pH before application was 5.4) and onto artificial skin (Bioskin Plate; produced by Beaulax), the pH was measured after 30 min. using a skin checker MJ-120 (produced by Sato Trading). The results are shown in Table 1.

TABLE 1

| Cloth | pH 30 min. after application |
|---|---|
| Skin (forearm inside) | 5.7 |
| Bioskin plate | 7.9 |

From these results, it can be seen that this skin is weakly acidic, and that a composition applied to the skin will become weakly acidic.

Examples 1 and 2, Comparative Examples 1 to 4

Oil in Water Emulsion Cosmetic Material (Sunscreen)

Oil in water emulsion cosmetic materials were obtained by mixing the components shown in Table 2 by the following manufacturing method.

(Manufacturing Method 1): Example 1 and Comparative Examples 1 to 4

Components (1) to (3) were heated and mixed to produce an oil phase. Furthermore, components (4) to (9) were heated and mixed to produce an aqueous phase. The oil phase and the aqueous phase were blended and emulsified at a regulated temperature (80° C.). Premixed components (10) to (14) were added to the emulsion and mixed, and then component (15) was mixed and then cooled to room temperature to obtain an oil in water type emulsion cosmetic material. Note, the amount of untreated titanium oxide of component (14) was adjusted to be the same amount as the titanium oxide which is the hydrophobic powder of component (13).

(Manufacturing Method 2): Example 2

Components (1) to (3) were heated and mixed to produce an oil phase. Furthermore, components (4) to (10) were heated and mixed to produce an aqueous phase. The oil phase and the aqueous phase were blended and emulsified at a regulated temperature (80° C.). Premixed components (11) to (14) were added to the emulsion and mixed, and then component (15) was mixed and then cooled to room temperature to obtain an oil in water type emulsion cosmetic material.

[Carboxylic Acid Modified Silicone (A1)]

The compound expressed by the following structural formula (A1) was used as the carboxylic acid modified silicone. Incidentally, the carboxylic acid modified silicone of structural formula (A1) contains only methyl hydrogen siloxy units where the sidechain part is expressed by SiH ($CH_3$)O, and can be produced by hydrosilylation reacting a methyl hydrogen polysiloxane that is capped on both ends of the molecular chain by a trimethylsiloxy group and undecylenoic acid, in the presence of a platinum catalyst, at a molar ratio of undecylenoic acid to silicon atom bonded hydrogen atoms of 1 or higher.

[Formula 9]

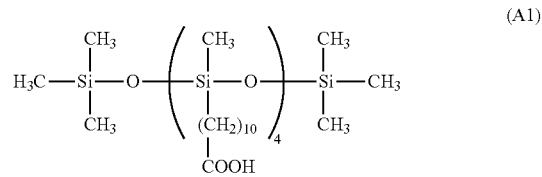

(A1)

In the following tests, the carboxylic acid modified silicone according to the aforementioned structural formula (A1) was used unless otherwise expressly noted.

TABLE 2

|  |  | Example 1 | Example 2 | Comparative Example 1 |
|---|---|---|---|---|
| 1 | Cetearyl alcohol/cetearyl glucoside (Note 1) | 8.00 | 8.00 | 8.00 |
| 2 | Tri(caprylic acid/capric acid) glyceryl | 9.00 | 9.00 | 9.00 |
| 3 | Tocopherol | 0.05 | 0.05 | 0.05 |
| 4 | Purified water | 52.15 | 52.15 | 52.15 |
| 5 | Dipotassium glycyrrhizinate | 0.10 | 0.10 | 0.10 |
| 6 | Xanthan gum | 0.30 | 0.30 | 0.30 |
| 7 | Glycerin | 2.00 | 2.00 | 2.00 |
| 8 | Potassium hydroxide | 0.12 | 0.12 | — |
| 9 | Phenoxyethanol | 0.40 | 0.40 | 0.40 |
| 10 | 1,3-butylene glycol | 14.00 | 14.00 | 14.00 |
| 11 | Carboxylic acid modified silicone (note 2) | 3.00 | 3.00 | — |
| 12 | PEG-12 dimethicone | — | — | — |
| 13 | Hydrogen dimethicone coated fine particles titanium oxide (Note 3) | 8.00 | 8.00 | 8.00 |
| 14 | Fine particle titanium oxide (Note 4) | — | — | — |
| 15 | Purified water | Balance | Balance | Balance |
|  | Total | 100.00 | 100.00 | 100.00 |
|  | pH | 8.1 | 8.1 | 7.8 |
|  | Evaluation Results |  |  |  |
|  | pH of skin after application | 5.3 | 5.2 | 5.1 |
|  | Feel of use (moist, fresh) | ◎ | ◎ | X |
|  | Dispersibility | ◎ | ○ | X |
|  | Water resistance | ○ | ○ | Δ |

|  |  | Comparative Example 2 | Comparative Example 3 | Comparative Example 4 |
|---|---|---|---|---|
| 1 | Cetearyl alcohol/cetearyl glucoside (Note 1) | 8.00 | 8.00 | 8.00 |
| 2 | Tri(caprylic acid/capric acid) glyceryl | 9.00 | 9.00 | 9.00 |

TABLE 2-continued

| # | Component | | | |
|---|---|---|---|---|
| 3 | Tocopherol | 0.05 | 0.05 | 0.05 |
| 4 | Purified water | 52.15 | 52.15 | 52.15 |
| 5 | Dipotassium glycyrrhizinate | 0.10 | 0.10 | 0.10 |
| 6 | Xanthan gum | 0.30 | 0.30 | 0.30 |
| 7 | Glycerin | 2.00 | 2.00 | 2.00 |
| 8 | Potassium hydroxide | — | — | 0.12 |
| 9 | Phenoxyethanol | 0.40 | 0.40 | 0.40 |
| 10 | 1,3-butylene glycol | 14.00 | 14.00 | 14.00 |
| 11 | Carboxylic acid modified silicone (note 2) | — | — | 3.00 |
| 12 | PEG-12 dimethicone | — | 3.00 | — |
| 13 | Hydrogen dimethicone coated fine particles titanium oxide (Note 3) | — | 8.00 | — |
| 14 | Fine particle titanium oxide (Note 4) | 5.98 | — | 5.98 |
| 15 | Purified water | Balance | Balance | Balance |
| | Total | 100.00 | 100.00 | 100.00 |
| | pH | 7.8 | 7.8 | 8.1 |
| | Evaluation Results | | | |
| | pH of skin after application | 4.8 | 4.7 | 5.2 |
| | Feel of use (moist, fresh) | ◯ | ◉ | ◉ |
| | Dispersibility | ◯ | ◯ | ◉ |
| | Water resistance | X | X | X |

(Note 1)
Product name: Montanov 68 (produced by Seppic)
(note 2)
Carboxylic acid modified silicone expressed by structural formula (A1)
(Note 3)
Product name: MTX-02 (produced by Teika)
(Note 4)
Product name: MT-500B (produced by Teika)

The oil in water emulsion cosmetic materials of Examples 1 and 2 and Comparative Examples 1 to 4 were evaluated for feel during use (moisture, freshness), dispersibility, and water resistance, using the following evaluation methods. The results are also shown in Table 2.

[Feel of Use]

The evaluation target (base layer cosmetic material) was applied to the face of 20 female panelists, and the feel of use during application (moisture, freshness) was evaluated by sense in accordance with the following criteria.

◉: 16 or more of the 20 panelists responded moist and refreshing
◯: 11 to 15 of the 20 panelists responded moist and refreshing
Δ: 6 to 10 of the 20 panelists responded moist and refreshing
x: 5 or fewer of the 20 panelists responded moist and refreshing

[Dispersibility]

Evaluation subject was stored for 30 days in a constant temperature chamber at 50° C., the dispersion condition of the hydrophobic powder was visually observed, and evaluation was made in accordance with the following criteria.

◉: The hydrophobic powder was uniformly dispersed even after 30 days of storage
◯: The hydrophobic powder agglomerated after 30 days had passed
Δ: The hydrophobic powder agglomerated after 15 days had passed
x: The hydrophobic powder agglomerated immediately after production, and was not dispersed in the aqueous phase

[Water Resistance]

0.5 mg/cm² of the evaluation target was applied uniformly to the inside forearm of 20 female panelists, and after 30 min., droplets of purified water were dripped, the droplets that formed on the surface were photographed, the contact angle was measured using the θ/2 method based on the shape, and evaluation was made by the following criteria.

◉: The average contact angle was 55° or higher
◯: The average contact angle was 40° or higher and less than 55°
Δ: The average contact angle was 20° or higher and less than 40°
x: The average contact angle was less than 20°

From the evaluation results of Examples 1 and 2 and Comparative Examples 1 to 4, Examples 1 and 2 that contained the hydrophobic powder together with the carboxylic acid modified silicone and the basic compound in the aqueous phase had excellent dispersibility of the hydrophobic powder, and the feel of use and the water resistance were also excellent, but Comparative Example 1 that did not contain a carboxylic acid modified silicone had poor dispersibility, and a uniform emulsion could not be obtained. Comparative Examples 2 and 4 that used untreated titanium oxide that was not hydrophobic treated and Comparative Example 3 that used PEG-12 dimethicone that is a polyether modified silicone in place of the carboxylic acid modified silicone had inferior water resistance. When Examples 1 and 2 were compared, Example 1 where the 1,3-butylene glycol which is a polyhydric alcohol, the hydrophobic powder, and the carboxylic acid modified silicone were premixed had superior dispersibility.

Example 3

Oil in Water Emulsion Cosmetic Material (Sunscreen)

An oil in water emulsion cosmetic material was obtained by mixing the components shown in Table 3 by the following manufacturing method.

(Manufacturing Method)

Phase A (components 1 to 5) was mixed, and the premixed phase B (components 6 to 12) were added and emulsified. After emulsifying, phase C (components 13 to 19) were added and mixed. Furthermore, premixed phase D (components 20 to 22) was added and mixed, and then phase E (component 23) was added and mixed, and then degassing was performed to obtain an oil in water emulsified cosmetic material.

TABLE 3

|   |    |                                                         | Example 3 |
|---|----|---------------------------------------------------------|-----------|
| A | 1  | Purified water                                          | 1.00      |
|   | 2  | Glycerin                                                | 1.90      |
|   | 3  | Citric acid                                             | 0.011     |
|   | 4  | Potassium hydroxide                                     | 0.10      |
|   | 5  | Isostearic acid (Note 5)                                | 1.00      |
| B | 6  | Tocopherol                                              | 0.05      |
|   | 7  | Triethylhexanoin                                        | 5.60      |
|   | 8  | Methyl hexyl palmitate                                  | 2.25      |
|   | 9  | Caprylyl methicone                                      | 2.25      |
|   | 10 | (dimethicone/vinyl dimethicone) cross polymer           | 1.26      |
|   | 11 | Cyclopentasiloxane                                      | 2.115     |
|   | 12 | Dimethicone                                             | 1.125     |
| C | 13 | Purified water                                          | 40.73     |
|   | 14 | Tetrasodium etidronate                                  | 0.08      |
|   | 15 | Dipotassium glycyrrhizinate                             | 0.10      |
|   | 16 | Potassium hydroxide                                     | 0.76      |
|   | 17 | Xanthan gum                                             | 0.40      |
|   | 18 | Pentylene glycol                                        | 2.00      |
|   | 19 | Phenoxyethanol                                          | 0.50      |
| D | 20 | 1,3-butylene glycol                                     | 14.00     |
|   | 21 | Carboxylic acid modified silicone (note 2)              | 3.00      |
|   | 22 | Hydrogen dimethicone coated fine particles titanium oxide (Note 3) | 8.00 |
| E | 23 | Purified water                                          | Balance   |
|   |    | Total                                                   | 100.00    |
|   |    | pH                                                      | 8.4       |

TABLE 3-continued

|   | Example 3 |
|---|-----------|
| Evaluation Results | |
| PH of skin after application | 6.2 |
| Feel of use (moist, fresh) | ◎ |
| Dispersibility | ◎ |
| Water resistance | ◎ |

(Note 5) Product name: Isostearic acid EX (produced by Higher Alcohol Industries)

The oil in water emulsion cosmetic material of Example 3 was evaluated for feel during use (moisture, freshness), dispersibility, and water resistance, using the aforementioned evaluation methods and evaluation criteria. The results are also shown in Table 3.

Based on the evaluation results of Example 3, it can be seen that improved water resistance can be achieved by using a salt of a higher fatty acid (isostearic acid) (condition of the salt is achieved by the presence of potassium hydroxide), and not using a hydrophilic surfactant (cetearyl alcohol and cetearyl glycoside used in Example 1).

Example 4 and Comparative Examples 5 and 6

Aqueous Foundation (2 Layer Separation Type)

Aqueous foundation cosmetic materials were obtained by mixing the components shown in Table 4 by the following manufacturing method.

(Manufacturing Method)

Phase A (components 1 to 6) was mixed to form the aqueous phase. Phase B (components 7 to 14) was premixed and added to phase A and mixed, and then phase C (component 15) was added and mixed to obtain an aqueous foundation.

TABLE 4

|   |    |                                                      | Example 4 | Comparative Example 5 | Comparative Example 6 |
|---|----|------------------------------------------------------|-----------|------------------------|------------------------|
| A | 1  | Purified water                                       | 60.00     | 60.00                  | 60.00                  |
|   | 2  | Glycerin                                             | 5.00      | 5.00                   | 5.00                   |
|   | 3  | Pentylene glycol                                     | 2.00      | 2.00                   | 2.00                   |
|   | 4  | Sodium chloride                                      | 0.40      | 0.40                   | 0.40                   |
|   | 6  | Potassium hydroxide                                  | 0.30      | 0.30                   | 0.30                   |
| B | 7  | 1,3-butylene glycol                                  | 14.00     | 14.00                  | 14.00                  |
|   | 8  | Carboxylic acid modified silicone (Note 2)           | 3.00      | —                      | 3.00                   |
|   | 9  | Hydrogen dimethicone coated fine particles titanium oxide (Note 3) | 8.00 | 8.00 | — |
|   | 10 | Fine particle titanium oxide (Note 4)                | —         | —                      | 5.98                   |
|   | 11 | Silicone coated titanium oxide (Note 6)              | 1.50      | 1.50                   | 1.50                   |
|   | 12 | Dimethicone coated red iron oxide (Note 7)           | 0.05      | 0.05                   | 0.05                   |
|   | 13 | Dimethicone coated yellow iron oxide (Note 8)        | 0.24      | 0.24                   | 0.24                   |
|   | 14 | Dimethicone coated black iron oxide (Note 9)         | 0.03      | 0.03                   | 0.03                   |
| C | 15 | Purified water                                       | Balance   | Balance                | Balance                |
|   |    | Total                                                | 100.00    | 100.00                 | 100.00                 |
|   |    | pH                                                   | 8.2       | 6.8                    | 8.3                    |
|   |    | Evaluation Results                                   |           |                        |                        |
|   |    | PH of skin after application                         | 6.4       | 5.5                    | 6.7                    |
|   |    | Feel of use (freshness)                              | ◎         | ◎                      | ◎                      |
|   |    | Dispersibility                                       | ◎         | X                      | Δ                      |
|   |    | Water resistance                                     | ◎         | Δ                      | X                      |

(Note 6) Product name: SA Titanium CR-50 (100%) (produced by Miyoshi Chemical)

(Note 7) Product name: SA Red R-516PS (100%) (produced by Miyoshi Chemical)

(Note 8) Product name: SA Yellow LL-100P (100%) (produced by Miyoshi Chemical)

(Note 9) Product name: SA Black BL-100P (100%) (produced by Miyoshi Chemical)

The aqueous foundation of Example 4 was evaluated for feel during use (moisture, freshness), dispersibility, and water resistance, using the following evaluation methods and evaluation criteria. The results are also shown in Table 4.

[Feel of Use]

The evaluation target (base layer cosmetic material) was applied to the face of 20 female panelists, and the feel of use during application (moisture, freshness) was evaluated by sense in accordance with the following criteria.

⊚: 16 or more of the 20 panelists responded moist and refreshing

◯: 11 to 15 of the 20 panelists responded moist and refreshing

Δ: 6 to 10 of the 20 panelists responded moist and refreshing x: 5 or fewer of the 20 panelists responded moist and refreshing

[Dispersibility]

Evaluation subject was stored for 30 days in a constant temperature chamber at 50°, the redispersion condition of the hydrophobic powder was visually observed, and evaluation was made in accordance with the following criteria.

⊚: Uniformly dispersed immediately after shaking no more than 10 times even after storing for 30 days ◯: Uniformly dispersed after shaking no more than 30 times even after storing for 30 days Δ: Would not uniformly disperse after shaking 30 times after storing for 30 days x: The hydrophobic powder agglomerated immediately after production, and was not dispersed in the aqueous phase

[Water Resistance]

0.5 mg/cm$^2$ of the evaluation subject was uniformly applied to the inside forearm of 20 female panelists, and after 30 min., water with a pH of 7.0 was carefully dripped, the water droplet that formed on the surface was photographed, the contact angle was measured by the θ/2 method based on this shape, and evaluation was performed by the following criteria.

⊚: The average contact angle was 55° or higher

◯: The average contact angle was 40° or higher and less than 55°

Δ: The average contact angle was 20° or higher and less than 40° x: The average contact angle was less than 20°

The aqueous foundation of Example 4 had excellent redispersibility of the hydrophobic powder after allowing to sit and separate, and the water resistance was favorable. With Comparative Example 5 that did not contain a carboxylic acid modified silicone, the hydrophobic powder did not uniformly disperse even when shaken, and could not be uniformly applied to the skin. Comparative example 6 that used hydrophilic untreated titanium oxide did not repel the water, and the water resistance was inferior.

Example 5

Aqueous Dispersion (for Sunscreen Cosmetic Material)

The components shown in the following Table 5 were mixed using the following manufacturing method to produce a hydrophobic fine particle titanium oxide aqueous dispersion.

(Manufacturing Method)

Components 4 and 5 were blended, and then components 1 to 3 were added, mixed, and dispersed therein to produce an aqueous dispersion.

TABLE 5

|   |   | Example 5 |
|---|---|---|
| 1 | 1,3-butylene glycol | 25.00 |
| 2 | Carboxylic acid modified silicone (note 2) | 5.00 |
| 3 | Hydrogen dimethicone coated fine particles titanium oxide (Note 3) | 30.00 |
| 4 | Potassium hydroxide | 0.16 |
| 5 | Purified water | Balance |
|   | Total | 100.00 |
|   | pH | 8.10 |

With the aqueous dispersion of Example 5, the hydrophobic fine particle titanium oxide uniformly dispersed in the water phase without aggregating.

Example 6

Oil in Water Emulsion Cosmetic Material Using Aqueous Dispersion

An oil in water emulsion cosmetic material was obtained using the aqueous dispersion of example 5 by mixing the components shown in Table 6 by the following manufacturing method.

(Manufacturing Method)

Components (1) to (3) were seated and mixed to produce an oil phase. Furthermore, components (4) to (9) were heated and mixed to produce an aqueous phase. The oil phase and the aqueous phase were blended and emulsified at a regulated temperature (80° C.). Component (10) was added and mixed, component (11) was mixed, and then cooled to room temperature to obtain an oil in water type emulsion cosmetic material.

TABLE 6

|   |   | Example 6 |
|---|---|---|
| 1 | Cetearyl alcohol and cetearyl glucoside | 8.00 |
| 2 | Tri(caprylic acid/capric acid) glyceryl | 9.00 |
| 3 | Tocopherol | 0.05 |
| 4 | Purified water | 52.15 |
| 5 | Dipotassium glycyrrhizinate | 0.10 |
| 6 | Xanthan gum | 0.30 |
| 7 | Glycerin | 2.00 |
| 8 | Potassium hydroxide | 0.12 |
| 9 | Phenoxyethanol | 0.40 |
| 10 | Aqueous dispersion of example 5 | 20.00 |
| 11 | Purified water | Balance |
|   | Total | 100.00 |
|   | pH | 8.10 |

With the oil in water emulsion cosmetic material of example 6, the hydrophobic fine particle titanium oxide could easily be uniformly dispersed in an outside water phase by using the aqueous dispersion, and water resistance was provided.

What is claimed is:

1. A cosmetic material comprising:
(A) a hydrophobic powder;
(B) a carboxylic acid modified silicone;
(C) a basic compound; and
(D) water;
wherein the (A) hydrophobic powder is a silicone coated/treated titanium oxide and is dispersed directly in and in contact with an aqueous phase;
wherein the (B) carboxylic acid modified silicone has the following structural formula (A):

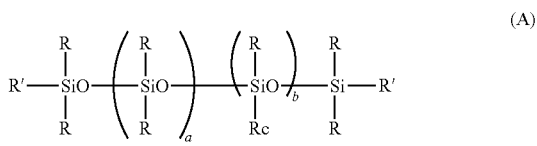

wherein Rc represents an organic group containing a carboxyl group expressed by the general formula: —$R^1$—($OR^2$)p-(O)w-$R^3$—COOH where $R^1$ represents a straight chain or branched alkylene group with 2 to 22 carbon atoms; $R^2$ represents a straight chain or branched alkylene group with 2 to 4 carbon atoms; $R^3$ represents a bond (—) or a straight chain or branched alkylene group with 1 to 22 carbon atoms; p represents a number between 0 and 200; and w represents a number of 0 or 1; R represents the same or different alkyl or alkoxy with 1 to 22 carbon atoms, or phenyl group; R' represents Rc or R; and a and b represent a number within a range of 0 or higher, where a+b represents a number within a range of 0 to 1000, with the proviso that when b=0, at least one of R' is Rc.

2. The cosmetic material according to claim 1, comprising 1 to 40 mass % of the (A) hydrophobic powder, with regard to the total mass of the cosmetic material.

3. The cosmetic material according to claim 1, comprising 0.01 to 20 mass parts of the (B) carboxylic acid modified silicone, with regard to 10 mass parts of the (A) hydrophobic powder.

4. The cosmetic material according to claim 1, wherein b>a, b>0, and a+b is a number within a range of 1 to 500.

5. The cosmetic material according to claim 1, comprising 20 to 95 mass % of the (D) water, with regard to the total mass of the cosmetic material.

6. The cosmetic material according claim 1, wherein the pH is within a range of 7.1 to 9.5.

7. The cosmetic material according to claim 1, further comprising (G) a polyhydric alcohol.

8. The cosmetic material according to claim 1, further comprising (E) an oil agent; alternatively further comprising 3 to 60 mass % of (E) an oil agent, with regard to the total mass of the cosmetic material.

9. The cosmetic material according to claim 1, further comprising (F) a salt of a higher fatty acid; alternatively further comprising 0.1 to 12 mass % of (F) a salt of a higher fatty acid, with regard to the total mass of the cosmetic material.

10. The cosmetic material according to claim 9, wherein the (F) higher fatty acid is one or more selected from the group consisting of isostearic acid, hexyldecanoic acid, and oleic acid.

11. The cosmetic material according to claim 1, further comprising (H) a water-soluble thickening agent.

12. The cosmetic material according to claim 9, not comprising a surfactant other than the (B) carboxylic acid modified silicone and the (F) salt of a higher fatty acid.

13. The cosmetic material according to claim 8, having a form of an oil in water emulsion composition.

14. A method of manufacturing the cosmetic material according to claim 1, comprising the step of:
blending the (A) hydrophobic powder, (B) carboxylic acid modified silicone, (C) basic compound, and (D) water to produce an aqueous dispersion where the (A) hydrophobic powder is dispersed in an aqueous phase.

15. A method of manufacturing the cosmetic material according to claim 7, comprising the step of:
blending the (A) hydrophobic powder, (B) carboxylic acid modified silicone, (C) basic compound, (D) water, and (G) polyhydric alcohol to produce an aqueous dispersion where the (A) hydrophobic powder is dispersed in an aqueous phase.

16. The method of manufacturing the cosmetic material according to claim 14, wherein the pH of the aqueous dispersion is within a range of 6.5 to 14.0.

17. A method of manufacturing the cosmetic material according to claim 7, comprising the steps of:
mixing the (G) polyhydric alcohol, (A) hydrophobic powder, and (B) carboxylic acid modified silicone to obtain a mixture; and
blending the (C) basic compound and (D) water into the mixture.

18. A method of manufacturing the cosmetic material according to claim 7, comprising the steps of:
mixing the (G) polyhydric alcohol, (A) hydrophobic powder, and (B) carboxylic acid modified silicone to obtain a mixture; and
blending the (C) basic compound and (D) water into the mixture to produce an aqueous dispersion with a pH in a range of 6.5 to 14.0 and where the hydrophobic powder is dispersed in an aqueous phase.

19. The method of manufacturing the cosmetic material according to claim 15, wherein the pH of the aqueous dispersion is within a range of 6.5 to 14.0.

* * * * *